United States Patent [19]

Tichy

[11] Patent Number: 4,913,133
[45] Date of Patent: Apr. 3, 1990

[54] HAND HELD PERIODONTIC TOOL

[76] Inventor: Edward Tichy, No. 21, Rte. 132, Woodbury, Conn. 06798

[21] Appl. No.: 241,011

[22] Filed: Sep. 2, 1988

Related U.S. Application Data

[63] Continuation-in-part of Ser. No. 212,569, Jun. 28, 1988.

[51] Int. Cl.[4] .......................... A61C 3/00; A61H 7/00
[52] U.S. Cl. .................................... 128/62 A; 433/142
[58] Field of Search .............. 433/142, 166; 128/62 A

[56] References Cited

U.S. PATENT DOCUMENTS

| | | | |
|---|---|---|---|
| 2,141,969 | 12/1938 | Benz | 128/62 A |
| 3,967,617 | 7/1976 | Kroick | 128/62 A |
| 4,343,839 | 9/1982 | Youngclaus | 128/62 A |

Primary Examiner—Robert Peshock
Attorney, Agent, or Firm—Chilton, Alix & Van Kirk

[57] ABSTRACT

A hand held periodontical tool preferably including a switch for adjusting the frequency of vibration, tabs accessible from the exterior of the housing for adjusting the vibration amplitude, and interchangeable end pieces, having a variety of tip members including side by side ribs that are separated from each other a distance smaller than at least one of the height and width dimensions of the ribs.

18 Claims, 10 Drawing Sheets

HAND HELD PERIODONTIC TOOL

CROSS REFERENCE TO RELATED APPLICATION

This is a continuation-in-part of copending application serial number 212,569, filed June 28, 1988.

BACKGROUND OF THE INVENTION

The present invention relates to a mechanical gum massaging device.

A variety of mechanical gum massaging devices are known in the art, particularly as exemplified by U.S. Pat. No. 3,967,617, "Mechanical Gum Massager" issued on July 6, 1976, in which a housing contains an eccentric fly wheel which is rotated by a motor, so that an angled end piece attached to the front of the housing is caused to vibrate on a circular or elliptical path, thereby stimulating the gums.

U.S. Pat. No. 4,205,664, "Tooth and Gum Massaging Implement", issued on June 3, 1980, and U.S. Pat. No. 3,563,233, "Sonic Dental Tool for Massaging Gums", issued on Feb. 16, 1971, disclose a variety of solid, flexible tips, or tips having discreet, spaced apart projections, for enhancing the stimulating effect of the gum massaging devices therein described.

U.S. Pat. No. 4,347,839, issued on Sept. 7, 1982, discloses a different type of mounting and actuating arrangement for the end piece of a mechanical gum massage device as compared with the overall arrangement shown in U.S. Pat. No. 3,967,617.

SUMMARY OF THE INVENTION

It is an object of the present invention to provide a hand held periodontic tool that is an improvement over the general type of gum massager disclosed in U.S. Pat. No. 3,967,617.

It is a more particular object to provide such improvements arising from the simplicity and effectiveness of a substantially tubular housing having a primary axis and an elongated shank projecting integrally from the upper end of the housing along a secondary axis which may be angled obliquely to the primary axis, the free end of the shank including a flexible tip for contacting the gum region in the mouth.

One improvement in accordance with the invention, enables a dental professional or the user to select from a variety of preventive maintenance prescription factors to customize the massaging of the gums with a given tool, such factors including a plurality of vibration frequencies, vibration amplitudes, and tip configurations.

Another improvement in accordance with the invention optimizes the relationship of height, separation, and width dimensions of ribs or the like on the resilient tip members projecting from the free end of the shank. Preferably, the tip is in the shape of a cone or spire, having a solid nose portion and a ribbed portion adjacent the nose portion. In one embodiment, the ribs are in the forms of slits cut into the tip surface.

The invention includes periodontical tools having a variety of tip orientations relative to the shank, shank axis orientation relative to the housing axis, tip vibration drive arrangements, and paths of tip movement. One such path of tip movement is along a portion of an arc centered at a location intermediate the ends of the shank.

BRIEF DESCRIPTION OF THE DRAWINGS

These and other objects and advantages are accomplished in accordance with the preferred embodiment of the invention as described below with reference to the accompanying drawings, in which.

DESCRIPTION OF THE PREFERRED EMBODIMENTS

Figures 1, 14:
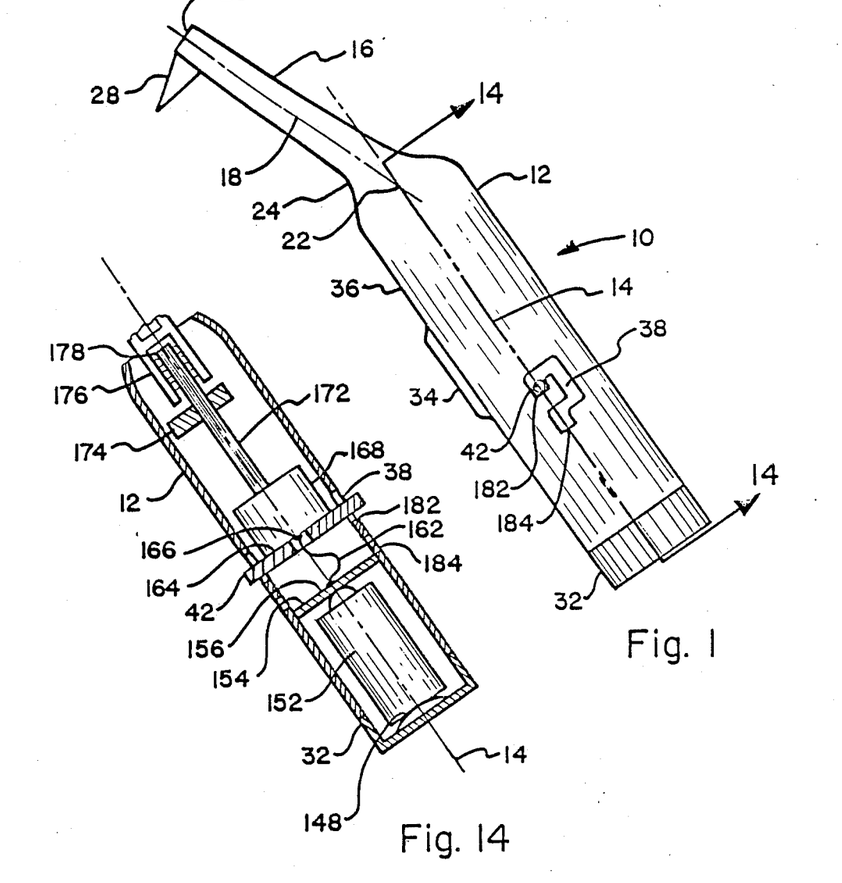
FIG. 1 is a side view of one embodiment of the periodontic tool with a conical tip member in accordance with the invention.
FIG. 14 is a section view taken along lines 14—14 of FIG. 1, showing a first embodiment of a drive subassembly wherein the vibration frequency and amplitude may be adjusted independently.

FIG. 1 shows a periodontic tool 10 having a substantially tubular housing or handle 12 disposed about a housing axis 14, and an integrally extending shank 16 having a shank axis 18 which intercepts the housing axis at a point 22 substantially near a transition neck portion 24 of the housing. At the free end 26 of the shank 16, an end piece in the form of a flexible tip member 28 projects substantially perpendicularly to the shank axis 18. At the lower end of the housing 12, a detachable cap 32 threadably closes off the substantially hollow interior of the housing 12. The interior of the housing contains a source of electric power, a motor, and associated components for imparting a vibratory action to the shank 16 and more particularly, to the tip 28. The interior actuating components may be of the type shown in U.S. Pat. No. 3,967,617, the disclosure of which is hereby incorporated by reference.

In accordance with one aspect of the invention, as shown in FIG. 1, a multi-speed actuating switch 34 is accessible to the user as the tool 10 is held in the hand, the switch having preferably three positions, the off position as shown, an intermediate position, and a maximum position 36. The intermediate and maximum positions provide two different motor speeds and thus two different vibrating frequencies of the tip member 28.

Also shown in FIG. 1 is another preferred feature, wherein the amplitude of vibration may also be adjusted by the user from outside the housing 12. In the implementation of this feature as indicated in FIG. 1, a two position slot or channel 38 provides two axially spaced notches in which an adjustment stem or tab 42 can be manipulated by the user to select a relatively higher or relatively lower position of the internal actuating components, thereby affecting the amplitude of the vibration of the tip member 28, as will be more fully explained below in connection with the description associated with FIG. 14.

The overall appearance and functionality of the periodontic tool as shown in FIG. 1, are based on the housing 12 and integral shank 16, and the relatively shallow angle, less than about 45 degrees and preferably less than 30 degrees, between the shank axis 18 and the housing axis 14.

The shank portion 16 may be formed in a substantially cylindrical, tapered, or rectangular cross section as shown in FIGS. 2-9. These figures illustrate several embodiments of the tip member which may be utilized in accordance with another feature of the present invention.

Figure 2:
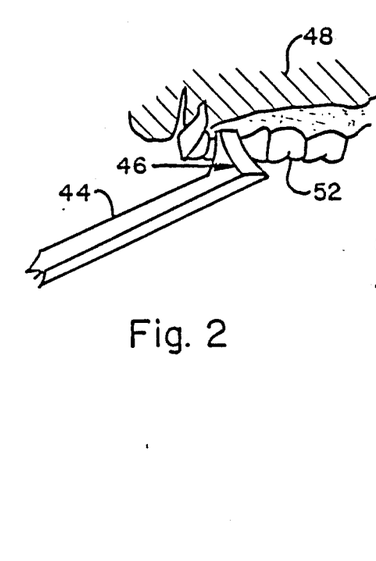
FIG. 2 is a perspective view showing a shank and associated first tip member in accordance with the invention.
Figures 3, 4:
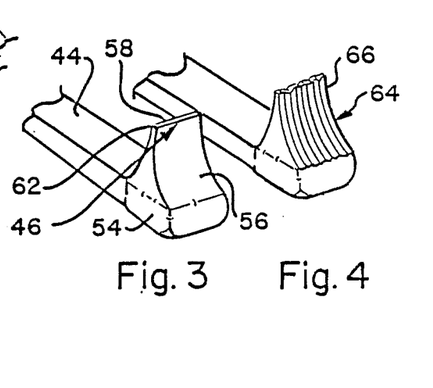
FIG. 3 is another perspective view of the wedge-shaped first tip member shown in FIG. 2.
FIG. 4 is perspective view of a second wedge-shaped tip member in accordance with the invention.

The tip member 46 shown in FIGS. 2 and 3 is adapted for gently yet actively stimulating and massaging the gums 48 in the vicinity of the teeth 52. The tip member 46 is substantially wedge-shaped, having a square or rectangular base portion 54 integral with or mounted on the shank 44, and a pair of slightly inwardly curved side walls 56 symmetric about a plane rising perpendicularly from the base 54 and transverse thereto. The active end, or peak, of the wedge-like tip member 46 has a substantially elongated rectangular portion 58 which, due to its narrow profile, is quite flexible to conform to the gum line. The associated pointed corners 62 can help loosen debris from the gum line. The tip member 46 is made of a flexible plastic or vinyl material of the type approved by the regulatory authorities for use in the human mouth.

FIG. 4 shows another embodiment wherein the tip member 64 has a profile or outline, that appears solid and closely resembles the wedge shape shown in FIG. 3, but upon close inspection is formed by a plurality of closely spaced individual, substantially triangular ribs 66. The ribs 66 are made from resilient, flexible plastic or vinyl, and are thus non-fibrous. In the tip member 64 shown in FIG. 4, and the other embodiments shown in FIGS. 5-9, the functionality of the tip is a hybrid of a solid tip and a brush tip, providing the advantages associated with each, and in addition, providing an enhanced massaging and stimulating action.

With reference to the directionally shown in FIG. 4, the ribbed tip members are formed from a unitary piece of non-fibrous material having a substantially solid base carried by the shank and a plurality of ribs extending substantially parallel to each other from the base, the ribs having a height dimension from the base to a peak in a direction 68 substantially perpendicular to the shank axis. The ribs define a separation dimension between the active peaks of adjacent ribs, in a direction 72 transverse to the height dimension. Each rib has a width dimension in a direction 70 perpendicular to the height and separation dimensions. The separation dimension for the ribs is smaller than at least one of the rib height and width dimensions and preferably smaller than both.

Figure 5:
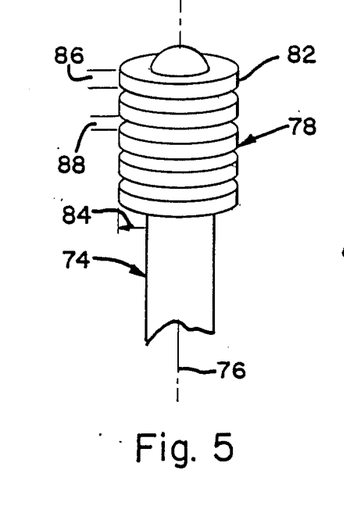
FIG. 5 is side view of a generally cylindrical third tip member.
Figure 6:
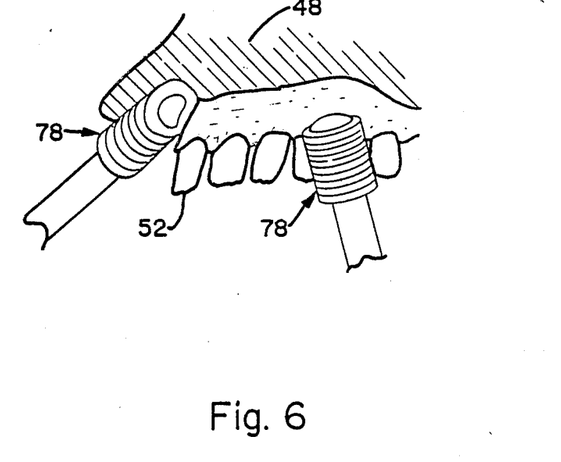
FIG. 6 is a schematic view showing the tip member of FIG. 5 in use.

FIG. 5 shows a third tip member embodiment 78 having a substantially cylindrical, rigid shank 74 with an associated shank axis 76. The tip member 78 is formed by a plurality of adjacent disc type flexible ribs coaxially supported on the shank 74. Each disc 82 has a height dimension 84, a width dimension 86, and a rib separation dimension 88, wherein the separation dimension 88 is less than the width dimension 86, as measured at the rib peaks. As shown in FIG. 6, with the ribs 78 made of a soft plastic or vinyl material, the tip member may be utilized either for point contact or broad area massaging action of the teeth and gums.

Figure 7:
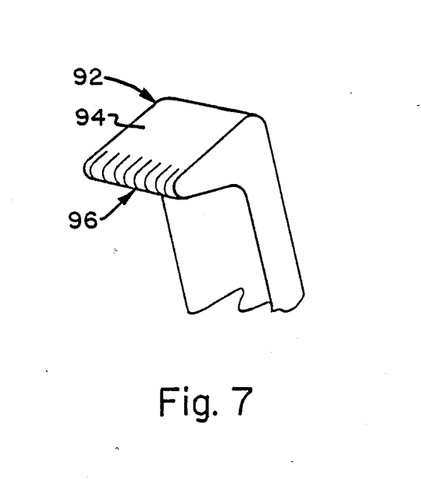
FIG. 7 is a perspective view of a wedge-shaped fourth tip member.
Figure 8:
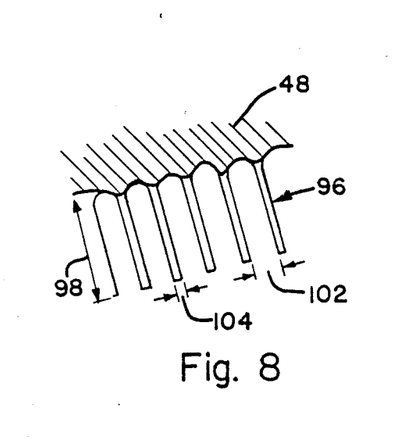
FIG. 8 is an enlarged detail of the rib ends of the tip member shown in FIG. 7.

FIG. 7 shows a fourth embodiment of a tip member 92, having a wedge shape wherein the base portion 94 of the tip member extends a substantial distance perpendicularly from the shank, and the ribs 96 are formed thereon by slitting the active end or peak of the tip member 92. As shown in FIG. 8, the height dimension 98 and the width dimension 102 are significantly larger than the separation distance 104. The very soft plastic material coupled with the slitting as shown, produces a gentle pinching action on the gums to stimulate blood flow. The overall shape of the tip member 92 is adapted to massage both the flat and pocket areas of the gums.

Figure 9:
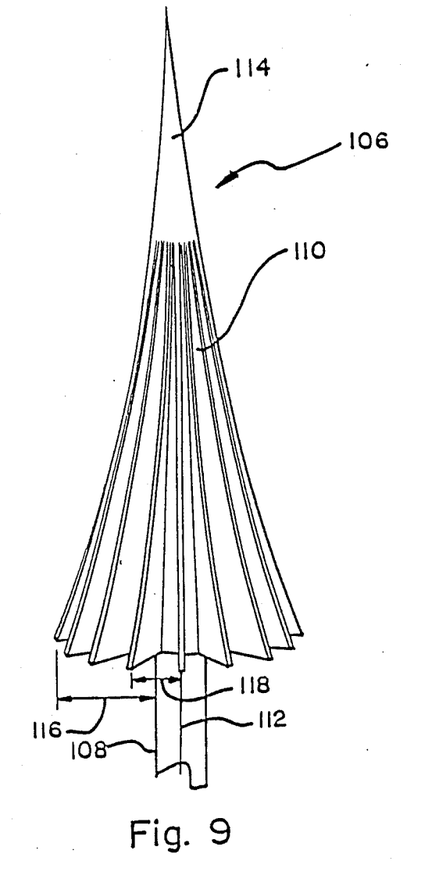
FIG. 9 is a side view of a spire-shaped fifth tip member.

FIG. 9 shows a fifth embodiment of a tip member 106, typically used with a cylindrical shank 108 having a shank axis 112. The tip member 106 is generally conical with a solid nose portion 114, typically made of vinyl, including a point projecting along shank axis 112. A trailing, ribbed portion of the tip member 106, provides inter-dental cleaning and massaging, by means of a spire-like splined arrangement of the ribs. The ribs 110 have a maximum height dimension 116, from shank or base 108 which decreases in the axial direction toward the nose 114. The ribs have a separation distance 118 which is smaller than the height dimension 116. The displacement of the ribs 110 during use varies proportionally with fluctuations of the amplitude and frequency of vibration. As shown in FIG. 9, the longest dimension of each rib is parallel to the shank axis 112, and is significantly larger than either the height 116 or separation dimensions 118. In the region of the ribs 110 immediately adjacent to the nose 114, the width dimension of each rib 110 can exceed the separation dimension between ribs.

Figure 10:
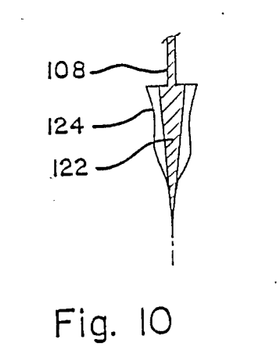
FIG. 10 is a section view of a variation of the tip member shown in FIG. 9.

FIG. 10 shows a variation of the tip member 106, in section, to illustrate that the shank or base 108 has an enlarged, conical extension portion 122, from which the ribs 124 project radially. The ribs preferably have a fluted or elongate-S profile that provides a more effective inter-dental cleaning action, particularly for concave or irregular proximal tooth surfaces.

Figure 15A:
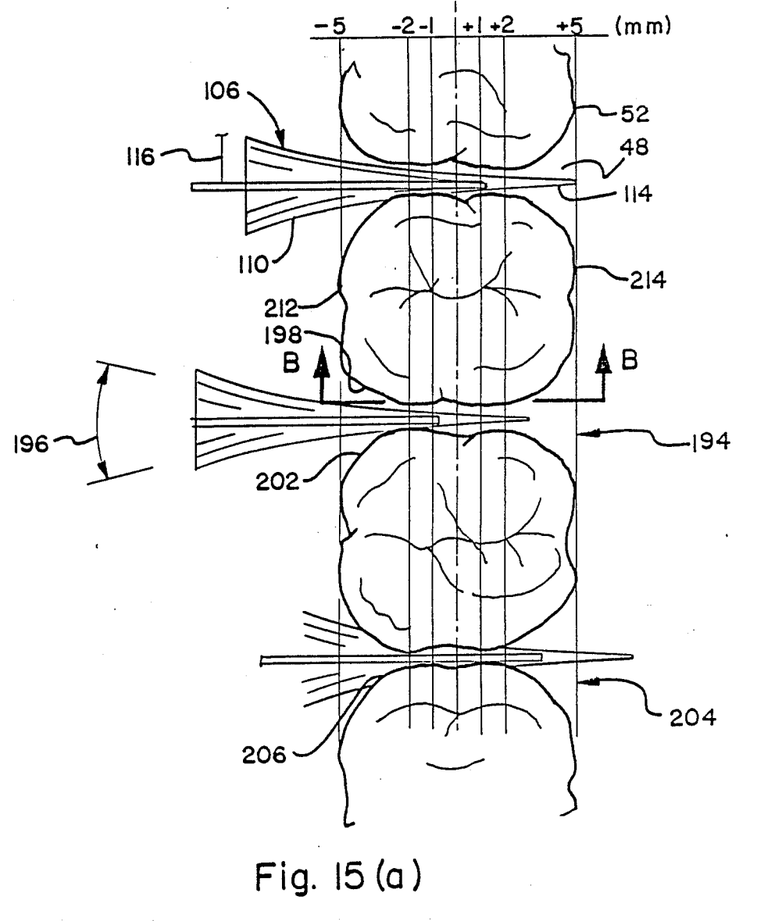
FIGS. 15(a) and 15(b) are schematic representations of the manner in which the tip shown in FIG. 9 is used to remove plaque in the nominal proximal area of the teeth.
Figure 15B:
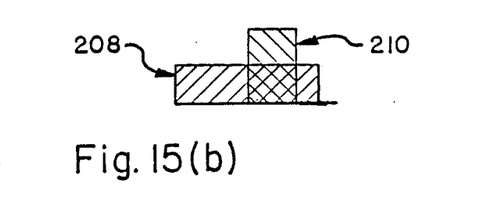

FIG. 15 illustrates how the tips shown in FIGS. 9 and 10 reach the nominal proximal area between the teeth that is not reachable by conventional tooth brushes and thus us effective for plaque control. FIG. 15(a) is a view looking downward on top of a row of teeth 52 and associated gum tissue 48, on which a row center line 192 and positive and negative distances perpendicular to such center line are indicated. The substantially solid nose portion 114 of the tip 106 enables the user, with relative light force on the tool handle, to insert the tip well past the center line. As the tip is inserted between the teeth, the vibrating action and the ribs 110 massage and help clean the gum tissue between the teeth. At the minimum depth position 194, the tip can be manually angled within the approximate range indicated at 196, so as to provide contact of the ribs 110 with the portions of the teeth indicated at 198, 202. At the maximum depth of insertion 204, the ribs 110 collapse to conform to the proximal surface contours 206 and are particularly effected in preventing the accumulation of plaque on these surfaces.

As shown in FIG. 15(b), the effective cleaning or contact area on the teeth 52 can be represented by two intersecting rectangles 208, 210, when a given tooth is viewed along lines B-B of FIG. 15(a). Particularly with the embodiment of the tool where the vibration amplitude can be adjusted by the user, the effective depth of penetration can be prescribed for considerations of cleaning effectiveness and comfort.

Preferably, the total length of the spire tip 106 is in the range of 10-15 mm, with the nose portion occupying about 2-4 mm, and the height 116 of the ribs at their widest part, i.e., at the base of the spire, being in the range of 1-3 mm, preferably about 2 mm.

If the user firmly grasps a tool of the type shown in FIG. 1 in the hand, and does not voluntarily move the hand, every location on the tip 106 will oscillate in a circle on a plane that is perpendicular to the housing axis 14. Preferably, the user will orient the tool handle 12 so that the spire tip penetrates the proximal area between two teeth, in the manner indicated in FIG. 15. Depending on the angular relationship of the tip 106 to the shank 16, and the shank to the handle 12, the path of tip vibration could be a circle on a plane parallel to the row center line 192 and parallel to the front and back surfaces 212, 214 of the tooth, (when the tip, shank, and handle axis are in a straight line), or a circle in a plane which is parallel to the row center line 192 and perpendicular to the front and back surface of the teeth, (when the tip axis is perpendicular to the handle axis). These extreme motion patterns, and those intermediate these extremes, can also be a part of the prescription for optimizing performance in a particular user's mouth.

Figures 16, 17:
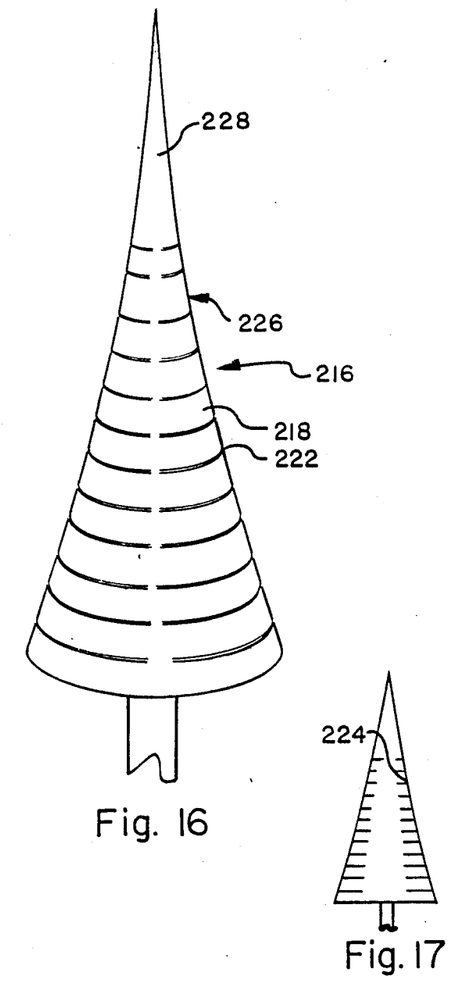
FIG. 16 is a side view of a spire shaped sixth tip member, having narrow slits annularly arranged transverse to the spire axis.
FIG. 17 is a section view of the tip shown in FIG. 16.
Figure 18:
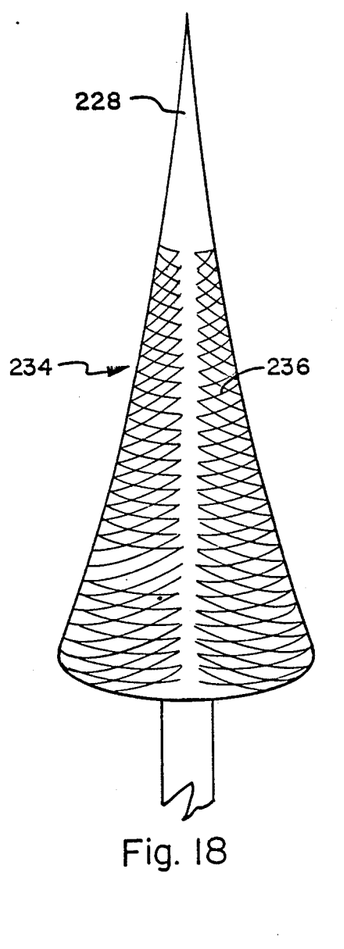
FIG. 18 is a side view of a spire shaped seventh tip member having slits in a diamond cross-hatch pattern.

FIGS. 16 and 17 show another embodiment of a conical or spire shaped tip 216, where the ribs 218 take the form, in effect, of the solid material remaining between very narrow slits or cuts 222, on the tip surface. The term "slit" as used herein, is intended to mean very narrow separation between portions of solid material, resulting from a cutting action or the like, in which a relatively small or zero amount of material is removed. In essence, this can be thought of as minimizing the separation distance between ribs 218. In the embodiment shown in FIGS. 16 and 17, the slits 222 are substantially annular, i.e., transverse to the tip longitudinal axis. Preferably, the slit height 224 as viewed in FIG. 17, is proportional to the diameter of the tip where the slit is located. Also, the trailing portion 226 of the tip, behind the substantially solid nose portion 228, can be stiffened slightly if desired, by cutting the slits through a total arc of slightly less than 360 degrees, leaving a web 232 as shown in FIG. 16. An embodiment 234 of the spire tip in which the slits are made in a diamond, cross-hatch pattern 236 is shown in FIG. 18.

Figures 11A, 11B, 11C, 12, 13:
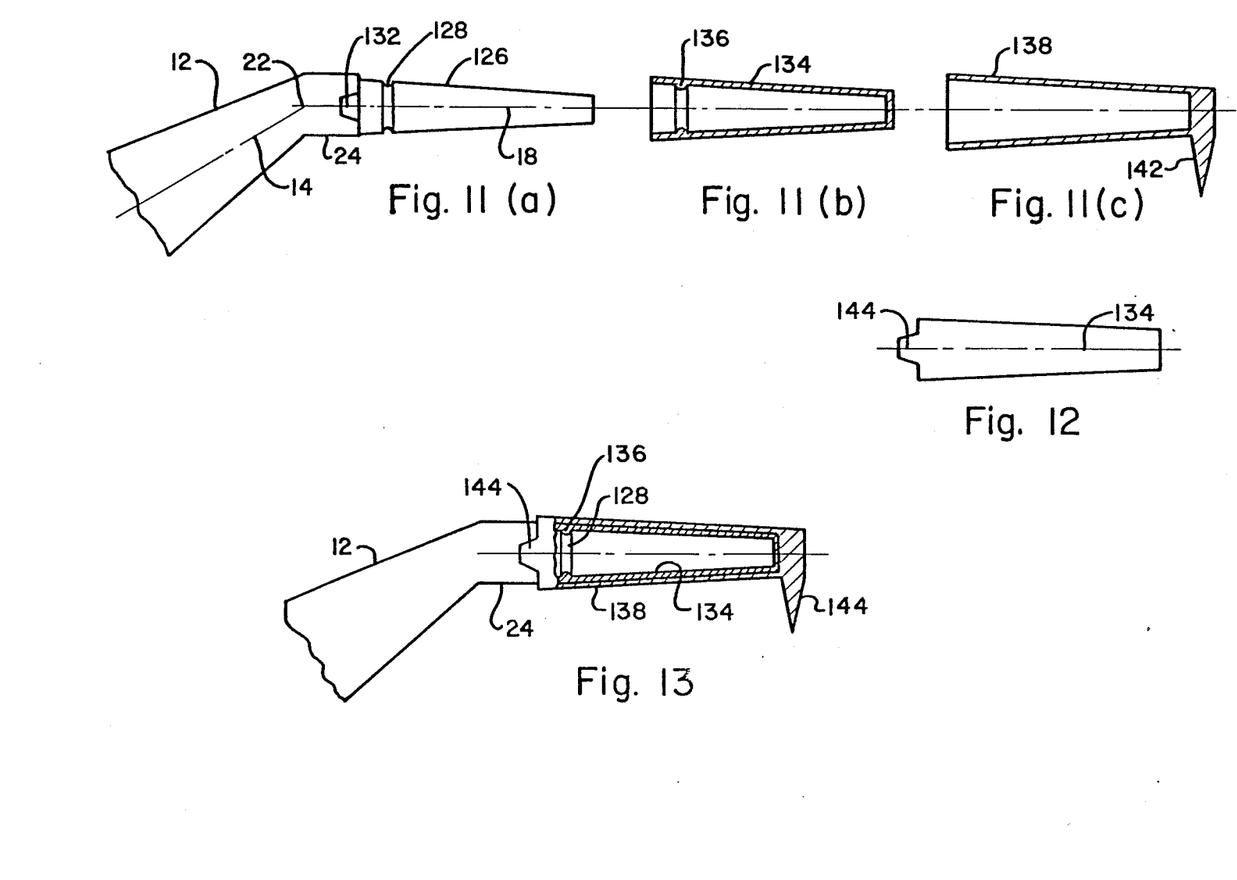
FIGS. 11(a)-(c) are side views, partly in section, showing an alternative embodiment of the shank, having interchangeable end pieces for a variety of tip members.
FIG. 12 is an exterior side view of the mold insert shown in FIG. 11(b)
FIG. 13 is an assembly view of the components shown in FIG. 11.

FIGS. 11-13 illustrate another feature of the invention wherein interchangeable tip members may be secured to the housing and shank, for example, of the type of tool shown in FIG. 1. The shank is formed as a tapered stem 126 and includes means, such as a circumferential groove 128, for receiving the body portion of a tip member which preferably comprises a combination of a molded inner insert 134 and an external sleeve member 138. The neck portion 24 of the housing, at the juncture with the stem 126, preferably includes a keyway 132 or the like for assuring proper orientation of the end piece combination 134, 138.

The end piece includes a tapered mold insert 134 having a hollow internal wall, except for an annular projection 136 for interacting with the groove 128 on the stem, to secure the end piece on the shank. The sleeve member 138 fits over the mold insert and is made from a vinyl material that, in effect, is molded around the insert. The remote end of the sleeve has the stimulator element, or tip member 142 formed thereon and can include any of the tip member embodiments described above. Exteriorly, as shown in FIG. 12, the molded insert 134 includes a key 144 projecting rearwardly, for engaging the keyway 132. Preferably, the mold insert is made from ABS plastic material or the like. Alternatively, the key 144 could be formed on the sleeve member 138, as shown in the assembled condition in FIG. 13.

FIGS. 1, 14, and 19-21 show another feature of the present invention, for permitting the user to select between two different vibration amplitudes. FIG. 14 is oriented as partial sectional view of the housing shown in FIG. 1. A coil or other spring member 148 is associated with the bottom of cap 132, for providing an upward bias on a source of electrical power, such as battery 152. A battery stop member 154 is supported by the housing wall 12 and includes a terminal 156 against which the positive terminal of battery 152 is biased by spring 148. A lead or other flexible conductor 162 is connected to terminal 156 at its lower end and passes through a central aperture 166 in platform 164. Platform 164 is preferably substantially circular, and has two diametrically opposed, projecting tabs 42, which pass through a pair of two position channels 38, on either side of the housing 12. The housing 12 can be molded in two longitudinal halves to accommodate the tabs during assembly.

An electrically driven, preferably two speed motor 168 is secured to the platform 164, and has a shaft 172 coaxial with the housing axis 14, and terminating in the vicinity of the neck region 24. An eccentrically mounted weight or flywheel 174 is secured to shaft 172 intermediate the free end 178 and the motor 168. Optionally, a bushing 176 or other mounting arrangement on the housing or shank interior may be provided at the free end of shaft 172.

As may be seen in conjunction with FIG. 1, the platform 164 and projecting tabs 42 as shown in FIG. 14, are in the upper position as defined by upper notch 182. In this position, the fly wheel 174 is relatively closer to the free end 26 of shank 16 and thus the free end 178 of the shaft 172 would be fully inserted within the bushing 176 (if provided). The second, lower position is achieved by grasping the tabs 42 with two fingers, lifting slightly, and following the path defined by channel 38 until the tabs are secured in the lower notch 184. This displaces the platform 164, motor 168, shaft 172, and flywheel 174 along housing axis 14 in a direction away from the shank free end 26. If provided, the bushing 176 should be long enough to retain the shaft free end 178 in the second position. The flexible lead 162 accommodates this movement of the platform 164 without stressing the electrical connections between the lead 156 and the motor 168. The two notch positions, 182, 184, thus define a different spatial relationship between the rotating fly wheel 174 and the shank free end 26, thereby defining two different amplitudes of vibration, for a given vibration frequency.

Figure 19:
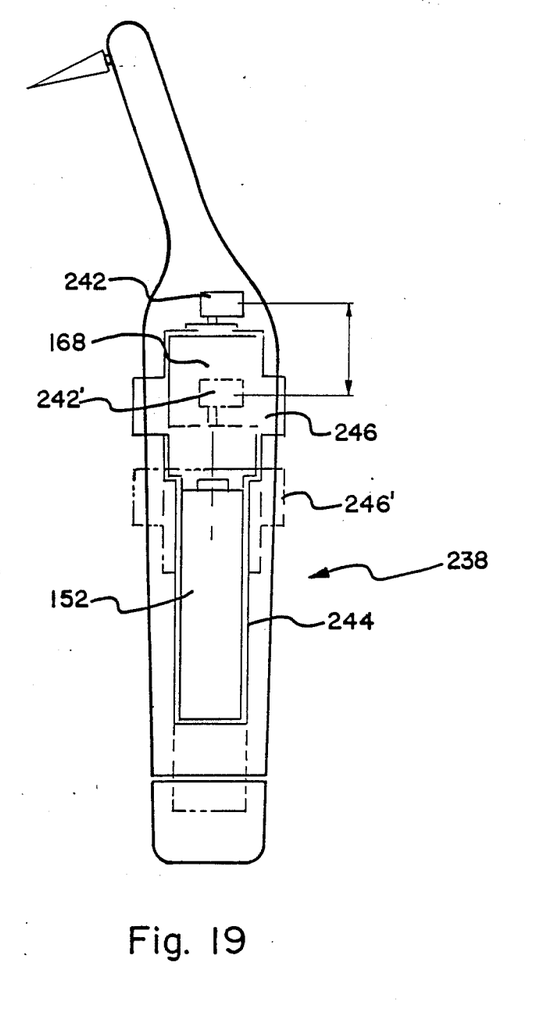
FIG. 19 is a schematic illustration of a second embodiment of a relocatable drive subassembly for adjusting the amplitude of vibration.

FIG. 19 shows another arrangement 238 for repositioning the eccentric fly wheel 242 along the handle axis. A cage or harness 244 of any convenient construction is adapted to contain or envelop the battery 152 and motor 168, i.e., to secure them in a fixed axial relationship to each other. As is conventional, means, such as the spring 148 acting on the lower end of the battery as shown in FIG. 1, or other similar structure, is provided to bias the battery and motor toward each other, as needed to maintain electrical contact and to take up any tolerances or slack that may lead to rattling within the handle during use. In a fashion similar to that described with reference to FIGS. 1 and 14, tabs and/or switches 246 project radially from the housing handle. The tabs are secured to the cage 244, such that as the tabs are repositioned axially from a first position to a second position 246' shown in phantom in FIG. 19, the cage and the fly wheel are axially repositioned to respective second positions 242'.

Figures 20, 21:
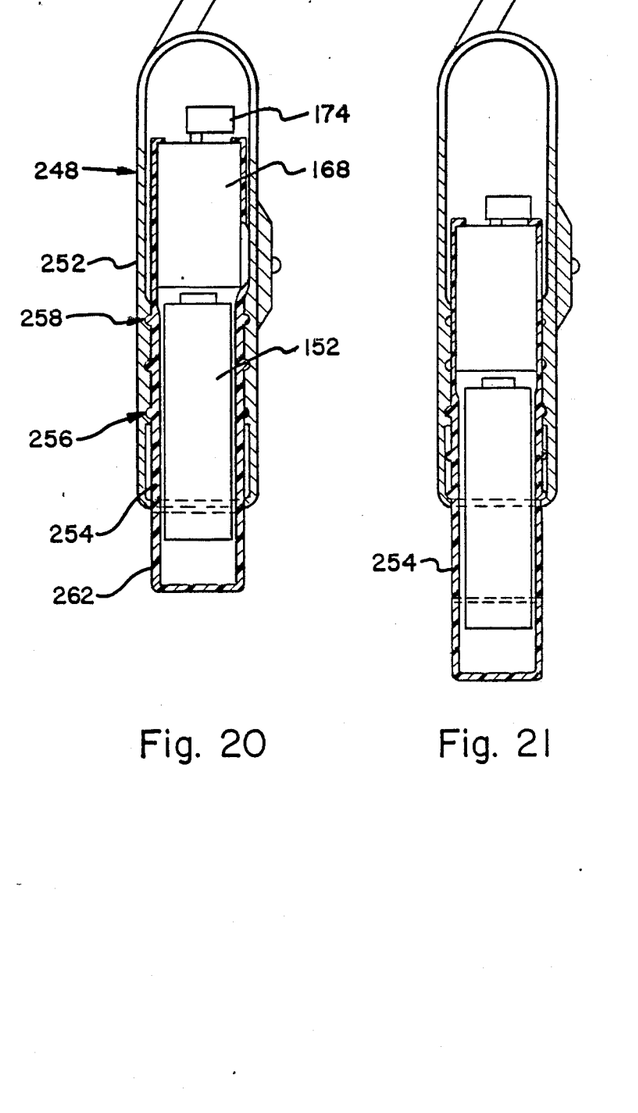
FIG. 20 is a schematic illustration of a third embodiment of a relocatable drive subassembly for adjusting the amplitude of vibration, in a first position.
FIG. 21 is similar to FIG. 20, except that the drive subassembly in a second, relocated position.

FIGS. 20 and 21 show another embodiment for adjusting the vibration amplitude of the tip, wherein the handle 248 has an upper portion 252 and a separate, relatively axially moveable lower portion 254. The lower portion 254 provides a cage or harness for the motor 168 and battery 152. Locator grooves or recesses 256 are provided on the lower interior of the upper portion 252 of the holder, and mating detents 258 or similar structure is provided on the exterior of the lower handle portion 254, for interacting with the recesses or grooves. A plurality of axially spaced grooves and detents are provided, which enable the user to select one of at least two axial positions of the lower holder portion 254 with a corresponding selection of at least two positions of the motor 168 and associated fly wheel 174. As described previously in connection with FIGS. 1, 14, and 19, any convenient biasing or retention structure is preferably added to maintain the motor and battery in firm, intimate contact or in fixed axial relation to each other, so that the entire drive train can be repositioned axially within the handle between the first and second positions as illustrated in FIGS. 20 and 21, respectively. In this embodiment, a twist off battery cap 262 is provided on the axially relocatable, lower portion 254 of the handle.

It should be appreciated that the linear advance between the upper and lower portions 252, 254 of the handle could be accomplished, although in a somewhat more complex arrangement, by a threaded or similar relationship between the handle parts. Thus the linear repositioning can be accomplished by twisting, for example, the lower portion relative to the upper portion or by a ring carried by the upper portion that is threadably engaged to the lower portion.

Figure 22:
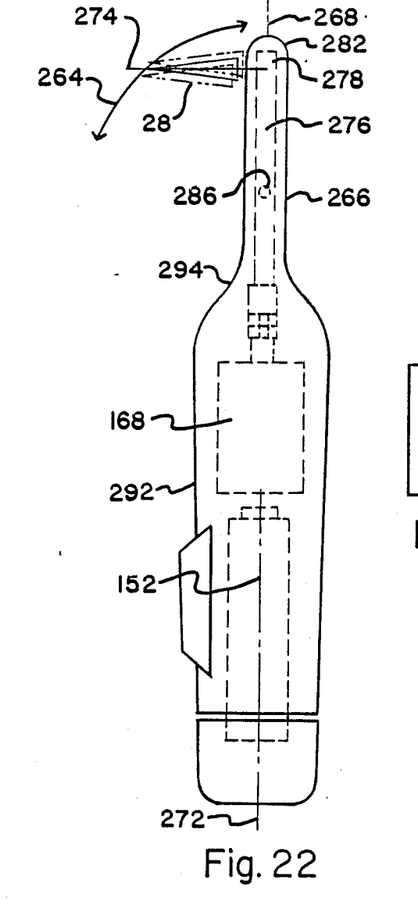
FIG. 22 is a schematic illustration showing a drive system adapted to impart a tip path of motion on an arc about a pivot axis in the shank which is oriented transversely to the shank axis.
Figure 23:
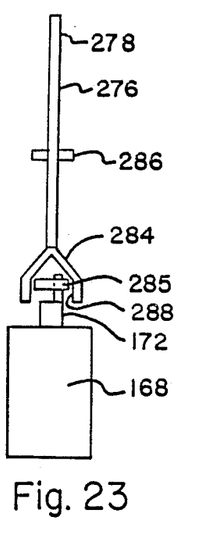
FIG. 23 is a detailed view of the relationship between the motor, eccentric cam, and arm of the preferred implementation of the drive system shown in FIG. 22.

FIGS. 22 and 23 illustrate another embodiment of the invention, wherein the tip 28 is actuated on a path of vibration along an arc 264 that is centered in the shank 266. In this embodiment, the shank axis 268 is coaxial with the handle axis 272, and the tip axis 274 is perpendicular to the shank axis, although this configuration can be varied somewhat while still incorporating the present feature of the invention. An arm member 276 is located in the interior of the shank and has a first end 278 near the free end 282 of the shank 266 to which the tip 28 is secured for movement relative to the free end of the shank. The other end 284 of the arm 276 is operatively connected to a cam wheel 285, or to other moving parts which produce cyclic displacement having a vector component that reciprocates transversely to the shank axis 268. A pivot pin 286 is connected through the arm 276 to the shank 266 intermediate the first 278 and second 284 ends of the arm. The pivot axis is transverse to the shank axis 276 and transverse to the displacement vector component mentioned above.

As shown in FIG. 23, the cam wheel 285 or equivalent produces movement of the arm second end 284, transverse to the shank axis which the wheel 285 reciprocates. Any convenient arrangement for connecting the rotational motion of shaft 172 to transverse reciprocating motion of cam 285 can be employed. Preferably, the arm lower end 284 and the cam wheel 285 or similar drive component are situated in the handle 292 immediately below the transition portion 294 to the integral shank 266.

Thus, in the preferred embodiment of the invention, a variety of prescription factors can be implemented in accordance with the instructions of a dental professional, or the desires of the user. As described herein, the user may select from two operative vibration frequencies, two different vibration amplitudes at each frequency, and a variety of interchangeable end pieces and associate tip members.

I claim:
1. A hand held periodontic tool comprising:
a substantially tubular handle having a primary axis and upper and lower ends;
an elongated shank projecting from the upper end of the handle along a secondary axis which is angled obliquely to the primary axis, and having a free end;
a tip member located on the free end of the shank and including a flexible tip for contacting the teeth and gum in the mouth, wherein the tip is made of a non-fibrous material in the form of a spire having a longitudinal axis, the spire including a lower portion formed by parallel, spaced apart longitudinal ribs and a solid, cone shaped upper nose portion terminating in a point on the spire axis.
2. In a hand held periodontical tool having a generally tubular handle defining a handle axis, a shank projecting from the handle and defining a shank axis, a flexible tip member projecting from the shank, and means for vibrating the tip member to interact with parts of the mouth, the improvement comprising:

said tip member having a generally conical shape and being formed from a resilient, non-fibrous material having a substantially solid base carried by the shank and a plurality of ribs extending from the base, substantially in parallel, each rib having a height dimension from the base to a peak in a direction substantially perpendicular to the base, a separation dimension between the peaks of adjacent ribs in a direction transverse to the height dimension, and a width dimension parallel to the separation dimension, the separation dimension being smaller than at least one of the height and width dimensions.

3. The hand held periodontic tool of claim 2, wherein the separation dimension is smaller than the height and width dimensions over the ribbed portion of the tip member that first contacts the mouth.

4. The hand held periodontic tool of claim 2, wherein the tip has the form of a spire having a longitudinal axis, the spire including a trailing portion formed by parallel ribs and a solid, nose portion terminating in a point on the spire axis.

5. The hand held periodontic tool of claim 4, wherein the separation dimension is smaller than the height and width dimensions over the ribbed portion of the tip member adjacent the nose portion.

6. The hand held periodontic tool of claim 4, wherein the ribs are parallel to the spire axis.

7. The hand held periodontic tool of claim 4, wherein the ribs are transversed to the spire axis.

8. The hand held periodontic tool of claim 2, wherein the tip has a substantially solid nose portion and the ribs are formed on a trailing portion adjacent the nose portion.

9. In a hand held periodontic tool having a generally tubular handle defining a handle axis, a shank projecting from the handle and defining a shank axis, a flexible tip member projecting from the shank, and means for vibrating the tip member to interact with parts of the mouth, the improvement comprising said tip member being formed from a resilient, non-fibrous material having a substantially conical shape and including an exterior surface having a multiplicity of slits therein.

10. The hand held periodontic tool of claim 9, wherein the slits are parallel to the longitudinal axis of the cone.

11. The hand held periodontic tool of claim 9, wherein the slits are transverse to the longitudinal axis of the cone.

12. The hand held periodontic tool of claim 9 wherein the slits are in a cross-hatch pattern.

13. The hand held periodontic tool of claim 9 wherein the cone includes a solid nose portion and the surface having the multiplicity of slits trails immediately adjacent the nose portion.

14. A tip member for a hand held vibrating periodontic tool, comprising:

a base portion for securing the tip member to the tool;

a ribbed portion made of non-fibrous flexible material connected to the base portion, the ribbed portion having the general profile of a truncated cone;

a generally conical, substantially solid nose portion made of non-fibrous flexible material, the nose portion extending from the ribbed portion and having a point defining a tip member central axis; and the nose portion and at least some of the ribbed portion being sized for axial insertion into and vibration within the nominal proximal area between teeth.

15. The tip member of claim 14, wherein the ribs are arranged substantially parallel to the axis, the ribs being separated from each other at any given location a distance which is less than the height dimension of the rib at that location.

16. The tip member of claim 15, wherein the total length of the nose and ribbed portion is in the range of 10–15 mm, and the maximum height of each rib is in the rage of 1–3 mm.

17. The tip member of claim 16, wherein the axial length of the nose portion is in the range of about 2–4 mm.

18. The tip member of claim 14, wherein the ribs are formed as cut slits.

* * * * *